United States Patent [19]

Stephen et al.

[11] Patent Number: 4,979,938
[45] Date of Patent: Dec. 25, 1990

[54] METHOD OF IONTOPHORETICALLY TREATING ACNE, FURUNCLES AND LIKE SKIN DISORDERS

[75] Inventors: Robert L. Stephen; Tomasz J. Petelenz; Stephen C. Jacobsen, all of Salt Lake City, Utah

[73] Assignee: Iomed, Inc., Salt Lake City, Utah

[21] Appl. No.: 350,227

[22] Filed: May 11, 1989

[51] Int. Cl.$^5$ ............................................. A61N 1/30
[52] U.S. Cl. ..................................... 604/20; 604/290; 128/798
[58] Field of Search ......................... 604/20, 289, 290; 128/639, 798, 799, 802, 803

[56] References Cited

U.S. PATENT DOCUMENTS

| | | | |
|---|---|---|---|
| 4,182,329 | 1/1980 | Smit et al. | 604/290 |
| 4,734,090 | 3/1988 | Sibalis | 128/798 |
| 4,767,402 | 8/1988 | Kost et al. | 604/290 |

FOREIGN PATENT DOCUMENTS

| | | | |
|---|---|---|---|
| 0007868 | 2/1987 | Japan | 604/20 |
| 2063072 | 6/1981 | United Kingdom | 128/803 |

Primary Examiner—David J. Isabella
Assistant Examiner—K. M. Reichle
Attorney, Agent, or Firm—Thorpe, North & Western

[57] ABSTRACT

A method is disclosed for treating acne, boils and similar skin disorders which are characterized by closed, blocked channels in the epidermis of the skin. The method comprises applying an applicator electrode on the skin of the person to be treated; providing a relatively small amount of water containing dissolved ions in contact with the applicator electrode and the affected tissue; applying a dispersive electrode on the skin of the person to be treated; applying a voltage differential to the applicator and dispersive electrodes such that the applicator electrode has a negative charge and the dispersive electrode has a positive charge; producing hydroxyl ions at the applicator electrode to develop a strongly alkaline solution therein, and driving the ions down the channels of the affected tissue by iontophoresis; continuing the application of the voltage differential to the applicator and dispersive electrodes for a time sufficient to disrupt the blockage of the channels in the affected tissue and to establish drainage from the channels.

12 Claims, 1 Drawing Sheet

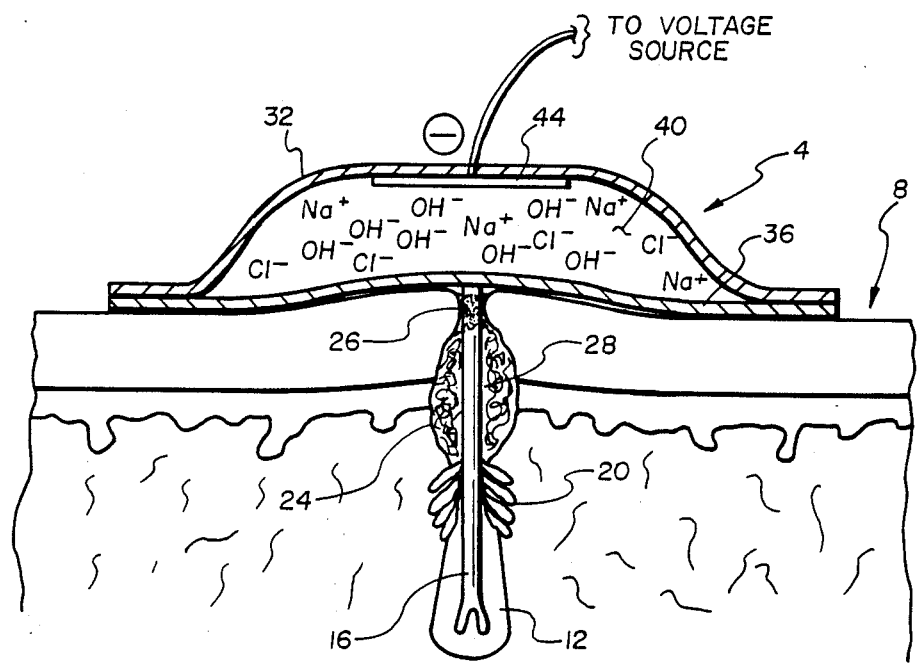

METHOD OF IONTOPHORETICALLY TREATING ACNE, FURUNCLES AND LIKE SKIN DISORDERS

BACKGROUND OF THE INVENTION

The present invention relates to a method of iontophoretically treating acne, furuncles (boils) and similar skin disorders which are characterized by obstructed channels such as hair follicles and sweat ducts in the skin tissue.

Iontophoresis is a technique for delivering ions into a person's skin or tissue by placing a solution, or other medium containing the ions, in contact or close proximity with the skin; the solution or medium containing the ions is typically carried by a first electrode pouch or receptacle. A second or dispersive electrode is placed against the skin within some proximity of the first electrode. Ions are caused to migrate from the ion carrying medium through the skin or tissue by the application of electric current of one polarity to the medium and by application of current of opposite polarity to the second electrode. The current is established by providing a sufficient voltage differential between the first and second electrodes.

The use of iontophoresis to deliver ions into a persons skin or tissue has been discussed in a number of prior art patents including U.S. Pat. Nos. 4,141,359, 4,166,457 and 4,752,285. Examples of electrodes which are useful for making electrical contact with the skin are described in U.S. Pat. Nos 3,862,633; 3,945,384; 3,973,557; 4,250,878; 4,419,092; and 4,477,971. The entire contents of the above-mentioned patents are incorporated herein by reference.

In conventional processes involving delivery of water-based medications into a person's skin by iontophoresis, electrolysis of the water produces hydroxyl ($OH^-$) and hydrogen ($H^+$) ions at the negative and positive electrodes, respectively. The reaction at the negative electrode may be represented as follows: $2H_2O \rightarrow H_2 \uparrow + 2OH^-$. The reaction at the positive electrode may be represented as: $2H_2O \rightarrow 4H^+ + O_2 \uparrow$. The hydroxyl and hydrogen ions act as competitors in the iontophoretic process of delivering ionized medications into the skin, resulting in fewer than the desired number of ions being delivered and at a slower rate. In other words, the hydrogen and hydroxyl ions represent unwanted process inhibiting byproducts at least in prior art applications and uses of iontophoresis.

Although iontophoresis is known and used as a mechanism for delivering medicaments into a person's skin or tissue so that the medicaments can operate both locally and systemically, there has been no suggestion, to applicants' knowledge, of using one of the previously unwanted byproducts of iontophoresis to treat skin disorders.

One skin disorder which, in many instances, has persistently resisted effective topical treatment is acne, especially cystic acne. Acne, as well as boils and like disorders, are typically caused by blockage of hair follicles. Such blockage results from a build up of organic material—dead skin cells, sebum secreted into the hair follicle from sebaceous glands located near the root of the follicle, bacteria and dirt. The full chain of events leading ultimately to cystic acne is as follows: (1) plugging of hair follicle giving rise to a "whitehead"; (2) oxidation of the tip of the "whitehead", turning it into a "blackhead"; (3) rupture of the hair follicle walls so that the accumulated contents thereof are discharged into the surrounding tissue to cause inflammation (this inflammation is called a papule or pimple); (4) accumulation of dead white blood cells (pus), bacteria and debris to form a pustule; (5) if pustule is not discharged spontaneously, enlargement (1 cm or more) of the inflamed area—known as a nodule; and (6) liquefaction of the nodule contents to include pus, blood and bacteria—this is cystic acne. Although the natural defense system of the body eventually brings about healing of cystic acne, oftentimes the skin is left with involution and scarring.

If the obstruction or blockage can somehow be cleared and the contents of the hair follicle disgorged at a point in time prior to cyst formation, the site(s) will drain and heal with minimal to no scarring. Even with cystic acne, discharge of the blockage will speed healing and there will be less tissue damage and less scarring.

Approaches to treating acne and like skin disorders have included the use of both topical and systemic medications. For example, desquamating agents, such as tretinoin ("Retin-A") and benzoyl peroxide ("Benzac"), have been used topically to cause peeling of the skin to facilitate follicular obstructions to allow drainage and healing. See Physicians' Desk Reference (PDR), 1989, pp. 1517 and 1518. Typical side effects from use of desquamating agents are inflammation, occasional burning of the skin and photo sensitivity.

Antibiotics, such as clindamycin and tetracycline have also been used topically to eradicate certain bacteria found on the skin, including those found in hair follicles. See pp. 1102 and 2153 of PDR. There are few side effects as a result of the use of topical antibiotics, but these drugs are fairly slow acting and of dubious effectiveness in treating nodular or cystic acne.

Systemic antibiotics (those administered orally), such as tetracycline and erythromycin, or the vitamin A dedrivative isotretinoin ("Acutane") are possibly the most effective medications in treating acne, but the side effects are likewise more serious. See p. 1711 of PDR. Some of these side effects ar detrimental alteration of the normal bacterial contents of the intestines, photosensitivity and temporary liver damage. With systemic isotretinoin, even more serious side effects may occur such as excessive dryness of the skin, eyes and mouth, inflammation of the intestines and fetal malformations.

SUMMARY OF THE INVENTION

It is a principal object of the invention to provide a novel method utilizing iontophoresis for the treatment of acne, boils and similar skin disorders which are characterized by both closed, blocked channels in the skin and underlying infection.

It is a further object of the invention to provide such a method, wherein a species of ions are generated for delivery into closed, blocked channels in the skin tissue being treated to eliminate the blockage.

It is also an object of the invention to provide a simple, easy-to-use method for treating acne, boils and like skin disorders where such method produces substantially no harmful side effects.

The above and other objects of the invention are realized in a specific illustrative embodiment of a process which utilizes iontophoresis to generate hydroxyl ions and to drive the ions into closed, blocked channels in the skin. The blocked channels will commonly be hair follicles which are blocked by foreign organic matter as discussed previously.

In accordance with the process of the present invention, an applicator electrode containing a water-based solution capable of producing hydroxyl ions is placed against the skin of the person to be treated, over the affected tissue. A dispersive electrode is also placed against the skin of the person, spaced from but in close proximity to the applicator electrode. A voltage differential is then applied to the applicator and dispersive electrodes such that the applicator electrode has a negative polarity and the dispersive electrode has a positive polarity. As a result, hydroxyl ions are produced at the applicator electrode and driven into the channels of the affected tissue by iontophoresis. The hydroxyl ions contact the organic matter of the blockage and break up the matter to allow the outflow of the channel contents.

BRIEF DESCRIPTION OF THE DRAWINGS

The above and other objects, features and advantages of the invention will become apparent from a consideration of the following detailed description presented in connection with the accompanying drawing which shows graphically a side cross-sectional view of an iontophoretic bioelectrode placed over an obstructed hair follicle to be treated using the method of the present invention.

DETAILED DESCRIPTION

In accordance with the present invention, a novel process is disclosed for treating acne, boils and other similar skin disorders which are characterized by closed, blocked channels, typically hair follicles, in the epidermis of the skin. In mild cases of such skin disorders, the skin tissue is able to disgorge the blockage before infection or other damage is done. However, in severe cases, such as acne and boils, the blockage is not readily disgorged and matter produced by the body's defense system enlarges the closed channels until rupture of the channel walls and spreading of the infected matter occurs. Eventually, an eruption takes place to allow drainage from the channel of the infected matter, and then healing, normally with attendant scarring, follows.

It has been found that the material blocking hair follicles can effectively be disrupted and expelled so as to establish drainage by treating the affected area of the skin using a procedure involving iontophoresis. Referring to the drawing, an applicator electrode 4 is shown overlying the skin 8 of the person to be treated, with the applicator electrode being positioned over an infected and inflamed hair follicle 12. The hair follicle 12 contains the root portion of a hair 16 and is in communication with sebaceous glands 20 which discharge sebum into the follicle. The follicle 12 is shown with an enlarged portion 24 containing organic matter 28 which is causing the swelling.

The applicator electrode 4 is of conventional design and includes an upper wall 32 and a bottom or base wall 36 joined at their perimeters to define an interior cavity 40 for holding a water-based solution for use in treating the infected hair follicle 12. The base wall 36 is an ion permeable membrane or other barrier capable of holding the solution while allowing the passage of ions. A conductive plate or sheet of material 44 is disposed on the upper wall 32 inside the cavity 40 and is coupled to a voltage source (not shown) so that a voltage of negative polarity is developed on the plate.

A dispersive electrode (not shown) is applied to the skin spaced from, but in close proximity to, the applicator electrode. A positive voltage is applied to this electrode, which may be of similar construction as the applicator electrode, to create a potential gradient between the applicator electrode and the skin.

A relatively small amount of water containing dissolved salt or other electrolyte capable of conducting an electrical current is placed in the applicator electrode. For example, a two to three cc of solution is generally sufficient for each treatment of a skin lesion. Advantageously, the solution is a dilute, unbuffered saline solution in order to supply a sufficient number of charge carriers for the passage of electric current. Applying a current of 1 to 10 milliamperes (preferably 3 to 4 ma) results in generation of hydroxyl ions which by reason of the negative potential on the plate 44, are caused to migrate from the solution in the cavity 40, through the base wall 36 and down the hair follicle 12, increasing pH value to approximately 10–12 pH units, a highly alkaline keratolytic solution. The ions tend to move along the path of least resistance which, in this case, is the hair follicle rather than through intact areas of skin. As time passes and more hydroxyl ions are produced, these ions become the primary ion current component.

The hydroxyl ions move down the hair follicle 12 where they contact and begin dissolving and breaking up the blockage 26 in a manner similar to the operation of lye on organic material. As a result, the blockage 26 is broken apart and disintegrated and the matter 28 is allowed to drain from the hair follicle 12.

The duration of the treatment, that is, the time period over which the voltage is applied to the electrodes, is between about 10 and 20 minutes. At the conclusion of the treatment, a drainage trace, in the form of a thin string of organic matter—mainly pus, will begin to form as drainage continues.

It is apparent from the above that with the present invention, both the time of treatment and the efficacy of delivery of the "medication" to the inflamed sites are significantly improved over prior art approaches. The time of treatment had been reduced from days, weeks and months to minutes and, with the ionic transport, the hydroxyl ion is delivered preferentially and deeply into hair follicles to disrupt blockages.

Although a preferred embodiment of the applicator electrode solution is a saline solution about 0.5 to 1.0 percent sodium chloride weight/volume it has been found that substantially any unbuffered electrolyte-containing water-based solution could be used. It is necessary that there be an electrolyte present in the water (and this could simply be hard water as opposed to deionized water) to initiate electric current and hence production of the hydroxyl ions and the iontophoresis process. The applicator electrode solution could also include other ionizable cleansing and healing agents which would aid in healing the lesion following drainage.

Examples of use of the method of the present invention follow:

EXAMPLE 1

Applicator iontophoretic electrodes containing three cc of water and about 0.9 percent sodium chloride weight/volume were placed over four large inflamed nodular acne lesions on the back of a patient and also over one developing boil on the neck of another patient.

A dispersive electrode was placed on the skin of the patients in close proximity to but spaced from the applicator electrodes by about several inches. A voltage of negative polarity was applied to the applicator electrodes and a voltage of positive polarity was applied to the dispersive electrode to develop a current of from 3 to 4 milliamperes. The currents were applied from twelve to fifteen minutes for each acne lesion and the developing boil. At the completion of the treatments, the pH in the applicator electrode had risen from an average of 6-7 units at the beginning to 10.5 units to 11.5 units at the conclusion of the treatments, and the skin located under the applicator electrodes had a "soapy" feel, resulting from the keratolytic effect of the alkaline solution which acts to saponify the outermost layers of skin. From 12 to 24 hours later, the tenderness and inflammation of all of the lesions and developing boil were reduced and small white threads of mucoid material extruding from the lesions and lying over the skin were present—these represented the draining from the infected hair follicles. Within 48 hours, the lesions were far along in the healing process and were essentially healed at the end of 72 hours.

EXAMPLE 2

Eight nodular/cystic acne lesions were treated in the manner described in Example 1 and seven other lesions were treated by an aqueous solution of the antibiotic clindamycin of about one percent weight/volume, using the same voltages, currents and treatment times. All fifteen lesions resolved within the times given in Example 1 and it was found that the lesions treated additionally with the clindamycin were healed no better than those treated only with saline solution (hydroxyl ion).

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

We claim:

1. A method for treating acne, furuncles and similar skin disorders which are characterized by blocked channels in the skin, said method comprising
   providing an iontophoresis device which includes an applicator electrode having a receptacle for receiving and holding an electrolytic water-based solution, a dispersive electrode, and a voltage source for providing a voltage of negative polarity to the applicator electrode and a voltage of positive polarity to the dispersive electrode;
   supplying an electrolytic, water-based solution to the receptacle of the applicator electrode;
   placing the applicator electrode and dispersive electrode on the skin of the person to be treated so that the applicator electrode is positioned over the skin affected by the disorder;
   operating the iontophoresis device so that a negative current is supplied from the voltage source to the applicator electrode and a positive current is supplied from the voltage source to the dispersive electrode to thereby produce hydroxyl ions in the solution which are caused to move into the channels of the skin affected by the disorder; and
   continuing the operation of the iontophoresis device for a time sufficient to disrupt the blockage of the channels in the skin affected by the disorder and establish drainage from the channels.

2. A method in accordance with claim 1 wherein said operating step comprises operating the iontophoresis device at a current level sufficient to render the solution in the applicator electrode alkaline to a pH value of about ten or above units.

3. A method in accordance with claim 1 wherein said placing step comprises placing the dispersive electrode on the skin in close proximity to the applicator electrode.

4. A method in accordance with claim 1 wherein said supplying step comprises supplying a solution of hard water containing mineral ions.

5. A method in accordance with claim 1 wherein said supplying step comprises supplying a dilute saline solution.

6. A method in accordance with claim 1 wherein said supplying step comprises supplying a solution which includes a cleansing agent.

7. A method in accordance with claim 1 wherein said supplying step comprises supplying a solution which includes an antibiotic.

8. A method in accordance with claim 1 wherein said supplying step comprises supplying about three cc of solution to the receptacle of the applicator electrode.

9. A method in accordance with claim 1 wherein said operating step comprises operating the iontophoresis device for a period of between about 10 and 20 minutes.

10. A method in accordance with claim 9 wherein the current is about 3 to 4 milliamps.

11. A method in accordance with claim 1 wherein the current supplied to the applicator and dispersive electrodes is from about 1 to 10 milliamps.

12. A method for treating acne, furuncles and like skin disorders which are characterized by blocked hair follicles in the skin, said method comprising
    placing an applicator electrode over the skin disorder of the person to be treated, said electrode holding an electrolytic, water-based solution,
    placing a dispersive electrode against the person's skin in a position spaced from but in close proximity to the position of the applicator electrode, and
    supplying a negative current to the applicator electrode and a positive current to the dispersive electrode to thereby produce hydroxyl ions in the solution in the applicator electrode which are caused to move into the hair follicles of the skin affected by the disorder,
    said supplying step continuing for a time sufficient to raise the pH value in the applicator electrode to a value of about 10 or more units and disrupt the blockage of the follicles.

* * * * *